(12) United States Patent
Bak et al.

(10) Patent No.: US 11,564,862 B2
(45) Date of Patent: Jan. 31, 2023

(54) MASSAGE APPARATUS PROVIDING PULSED ELECTROMAGNETIC FIELD

(71) Applicant: BODYFRIEND CO., LTD., Seoul (KR)

(72) Inventors: Sanghyun Bak, Seoul (KR); Woongchul Kang, Gyeonggi-do (KR); Soohyun Cho, Seoul (KR); Chuljin Jeon, Seoul (KR); Deokhyun Kong, Seoul (KR)

(73) Assignee: BODYFRIEND CO., LTD., Seoul (KR)

( * ) Notice: Subject to any disclaimer, the term of this patent is extended or adjusted under 35 U.S.C. 154(b) by 620 days.

(21) Appl. No.: 16/325,943

(22) PCT Filed: Aug. 29, 2017

(86) PCT No.: PCT/KR2017/009453
§ 371 (c)(1),
(2) Date: Feb. 15, 2019

(87) PCT Pub. No.: WO2018/044054
PCT Pub. Date: Mar. 8, 2018

(65) Prior Publication Data
US 2019/0201280 A1 Jul. 4, 2019

(30) Foreign Application Priority Data

Aug. 30, 2016 (KR) .................. 10-2016-0111022

(51) Int. Cl.
*A61H 23/02* (2006.01)
*A61H 7/00* (2006.01)
(Continued)

(52) U.S. Cl.
CPC .......... *A61H 23/0218* (2013.01); *A61H 7/00* (2013.01); *A61H 23/00* (2013.01); *A61H 23/02* (2013.01);
(Continued)

(58) Field of Classification Search
CPC .... A61H 23/02; A61H 23/0218; A61H 39/04; A61H 2039/005; A61H 2201/0149; A61H 2201/10; B60N 2/976
(Continued)

(56) References Cited

U.S. PATENT DOCUMENTS 5,084,003 A * 1/1992 Susic ................. A61H 23/0218
600/13
6,660,000 B2 * 12/2003 Neuberger ........... A61B 18/203
606/9

(Continued)

FOREIGN PATENT DOCUMENTS

EP 1629819 A1 3/2006
JP 3051342 U 8/1998
(Continued)

OTHER PUBLICATIONS

English translation of JP 6450909B2, IP.com (Year: 2019).*

*Primary Examiner* — Margaret M Luarca
*Assistant Examiner* — Cana A Gallegos
(74) *Attorney, Agent, or Firm* — Bridgeway IP Law Group, PLLC; Sang Ho Lee; Hyun Woo Shin (57) ABSTRACT

A massage apparatus providing a pulsed electromagnetic field may comprise: a massage unit which comprises a mount frame provided so as to be movable along the body of a user, and an acupressure module protrudingly provided to the mount frame so as to apply pressure to the body of the user; a pulsed electromagnetic field generator which is
(Continued)

provided to the mount frame so as to be independent from the acupressure module, and which generates a pulsed electromagnetic field by means of power applied thereto; and a controller which controls the operation of the acupressure module or the generation of the pulsed electromagnetic field. According to such massage apparatus, a pulsed electromagnetic field may be generated by having the pulsed electromagnetic field generator be provided to the massage unit so as to be separate from the acupressure module or air cells performing a massaging operation. In addition, an effect such as body tissue cell activation or damaged cell healing of the pulsed electromagnetic field may be provided when the massaging operation is being performed. Thus, compared to when only a pulsed electromagnetic field is provided without a massaging operation, or when only a continuous electromagnetic field is provided, fatigue of a user may be alleviated, or a disease or illness treatment or prevention effect may be doubled. In addition, since the pulsed electromagnetic field generator is arranged so as to be independent from the acupres sure module or air cells, the range of effects of the electromagnetic field may be expanded so as to include providing a pulsed electromagnetic field to even nearby sites to which pressure is not applied by the acupressure module or air cells, and since the pulsed electromagnetic field generator may be independently detached or replaced, costs for managing the massage apparatus may be reduced.

17 Claims, 10 Drawing Sheets

(51) Int. Cl.
　　　　*A61H 23/00*　　　　(2006.01)
　　　　*A61N 1/32*　　　　(2006.01)
　　　　*A61H 39/04*　　　　(2006.01)
　　　　*A61H 39/00*　　　　(2006.01)

(52) U.S. Cl.
　　　　CPC ............... *A61H 39/04* (2013.01); *A61N 1/32* (2013.01); *A61H 2039/005* (2013.01); *A61H 2201/0149* (2013.01)

(58) Field of Classification Search
　　　　USPC ........................................ 600/13, 14; 606/12
　　　　See application file for complete search history.

(56) References Cited

U.S. PATENT DOCUMENTS

| | | | | |
|---|---|---|---|---|
| 6,984,228 | B2* | 1/2006 | Anderson | A61B 5/0071 600/475 |
| 2004/0133251 | A1* | 7/2004 | Altshuler | A61B 18/203 607/88 |
| 2004/0158176 | A1* | 8/2004 | Park | A61H 39/04 601/18 |
| 2007/0016119 | A1* | 1/2007 | Inada | A61H 9/0078 601/151 |
| 2007/0093798 | A1* | 4/2007 | DeBenedictis | A61B 18/203 606/9 |
| 2007/0239089 | A1* | 10/2007 | Chiu | A61H 15/0078 601/99 |
| 2012/0022374 | A1* | 1/2012 | Weth | A61H 23/0218 601/15 |
| 2014/0343467 | A1* | 11/2014 | Fukuyama | A61H 9/0078 601/98 |
| 2017/0348180 | A1* | 12/2017 | Inada | G06Q 10/20 |

FOREIGN PATENT DOCUMENTS

| | | | |
|---|---|---|---|
| JP | 2001-046524 | A | 2/2001 |
| JP | 2001-104424 | A | 4/2001 |
| JP | 2004/0158176 | A | 6/2004 |
| JP | 2005-102919 | A | 4/2005 |
| JP | 2007-259882 | A | 10/2007 |
| JP | 2009-247547 | A | 10/2009 |
| JP | 5036249 | B2 | 9/2012 |
| JP | 2014-100181 | A | 6/2014 |
| JP | 2016-144546 | A | 8/2016 |
| JP | 6450909 | B2 * | 1/2019 |
| KR | 10-2014-0137212 | A | 12/2014 |

* cited by examiner

MASSAGE APPARATUS PROVIDING PULSED ELECTROMAGNETIC FIELD

TECHNICAL FIELD

The disclosure relates to a massage apparatus, and more particularly, to a massage apparatus providing a pulsed electromagnetic field (PEMF).

BACKGROUND ART

With a recent trend of well-being or a five-day workweek, a great deal of time and money are invested to improve our physical health, and people's perception of health care, health management, and health promotion is increasing regardless of sex or age. In particular, many people receive diagnoses or advice from experts in medical facilities, such as hospitals, for the purpose of an early detection or prevention of disease and are trying to manage, maintain, or improve their health using non-medical facilities such as sports clubs.

Further, apparatuses used to maintain or improve their health and fitness or overcome fatigue and relieve stress at home or at health clubs, for example, an exercise machine, such as a running machine, and a massage apparatus, have been developed and widely used in real life.

Massage is one auxiliary medical treatment for aiding blood circulation and relieving fatigue by sweeping, massaging, pushing, pulling, tapping, or moving a body with a hand or special apparatus. An apparatus for performing massage by a mechanical device is referred to as a massage apparatus, and various mechanical elements for an effective massage are used in the massage apparatus.

A massage chair type of massage apparatus, on which a user sits comfortably and receive a massage, is mainly used as such a massage apparatus that has a seat part, a backrest part, an armrest part, a leg massage part, and the like such that the user sits on the massage apparatus comfortably and can receive the massage. Each part has a massage unit which performs massage while moving along the user's spine, hips, thighs, calves, arms, and the like.

However, a massage unit of the conventional massage apparatus performs only the function of simply massaging or tapping a body so as to provide the effect of relieving fatigue of the muscles of the body and cannot provide the effect of treating or preventing the user's diseases or conditions.

DISCLOSURE

Technical Problem

The disclosure is directed to providing a massage apparatus that generate a pulsed electromagnetic field (PEMF) while performing a massaging operation.

Technical Solution

One aspect of the disclosure provides a massage apparatus that provides a pulsed electromagnetic field in order to solve the above problems.

The massage apparatus that provides a pulsed electromagnetic field includes a massage unit including a mount frame provided to be movable along a user's body and acupressure modules provided to protrude from the mount frame so as to apply pressure to the user's body, a pulsed electromagnetic field generator provided on the mount frame independently of the acupressure module and configured to generate a pulsed electromagnetic field by means of power applied thereto, and a controller configured to control operation of the acupressure module or generation of the pulsed electromagnetic field.

The pulsed electromagnetic field generator may be provided as a plurality of pulsed electromagnetic field generators.

The plurality of pulsed electromagnetic field generators may include pulsed electromagnetic field generators having different sizes or shapes.

The pulsed electromagnetic field generator may be disposed between the acupressure modules.

The controller may control at least one among a time when the pulsed electromagnetic field is generated, a time when the generation of the pulsed electromagnetic field is terminated, a frequency, a period, a width, an intensity, and a shape thereof.

The controller may perform control such that the pulsed electromagnetic field is generated in conjunction with the operation of the acupressure module.

The controller may control the generation of the pulsed electromagnetic field on the basis of at least one among a location, a moving speed, a massage mode, and an elapsed massage time of the massage unit.

The pulsed electromagnetic field generator may include a guide member provided in a cone shape with a diameter becoming greater towards the user's body so as to guide the generated pulsed electromagnetic field towards the user's body.

The controller may perform control such that a pulsed electromagnetic field of 5 to 15 Hz is generated.

Another aspect of the disclosure provides a massage apparatus that provides a pulsed electromagnetic field including an air cell provided in a housing so as to apply pressure to a user's body while being repeatedly expanded and contracted by air, a pulsed electromagnetic field generator provided on a rear surface of the housing independently of the air cell and configured to generate a pulsed electromagnetic field by means of power applied thereto, and a controller configured to control an operation of the air cell or generation of the pulsed electromagnetic field.

Advantageous Effects

According to the above-described massage apparatus, a pulsed electromagnetic field can be generated by having a pulsed electromagnetic field generator provided on a massage unit independently of an acupressure module or air cells for performing a massaging operation.

In addition, while the massaging operation is performed, an effect due to a pulsed electromagnetic field, such as activation of cells included in cellular tissue or healing of damaged cells, may be provided. Thus, as compared to when only a pulsed electromagnetic field is provided without a massaging operation, or when only a continuous electromagnetic field is provided, an effect of alleviating a user's fatigue or treating or preventing diseases or conditions thereof can be highly increased.

In addition, since the pulsed electromagnetic field generator is arranged independently of the acupressure module or the air cells, the range of the effect caused by an electromagnetic field can expand so as to include providing a pulsed electromagnetic field even to nearby sites to which pressure is not applied by the acupressure module or the air cells, and, since the pulsed electromagnetic field generator can be independently attached to the massage apparatus, detached from the massage apparatus, or replaced with new one, costs for managing the massage apparatus can be reduced.

MODES OF THE INVENTION

Exemplary embodiments described in the present specification and elements shown in the drawings are purely illustrative, and it will be understood that various modifications can be made to replace the embodiments and drawings at the time of filing of the present application.

A massage apparatus providing a pulsed electromagnetic field will hereinafter be described in detail with reference to the accompanying drawings according to the following exemplary embodiments described below. Like numerals refer to like elements throughout the drawings.

Figure 1:
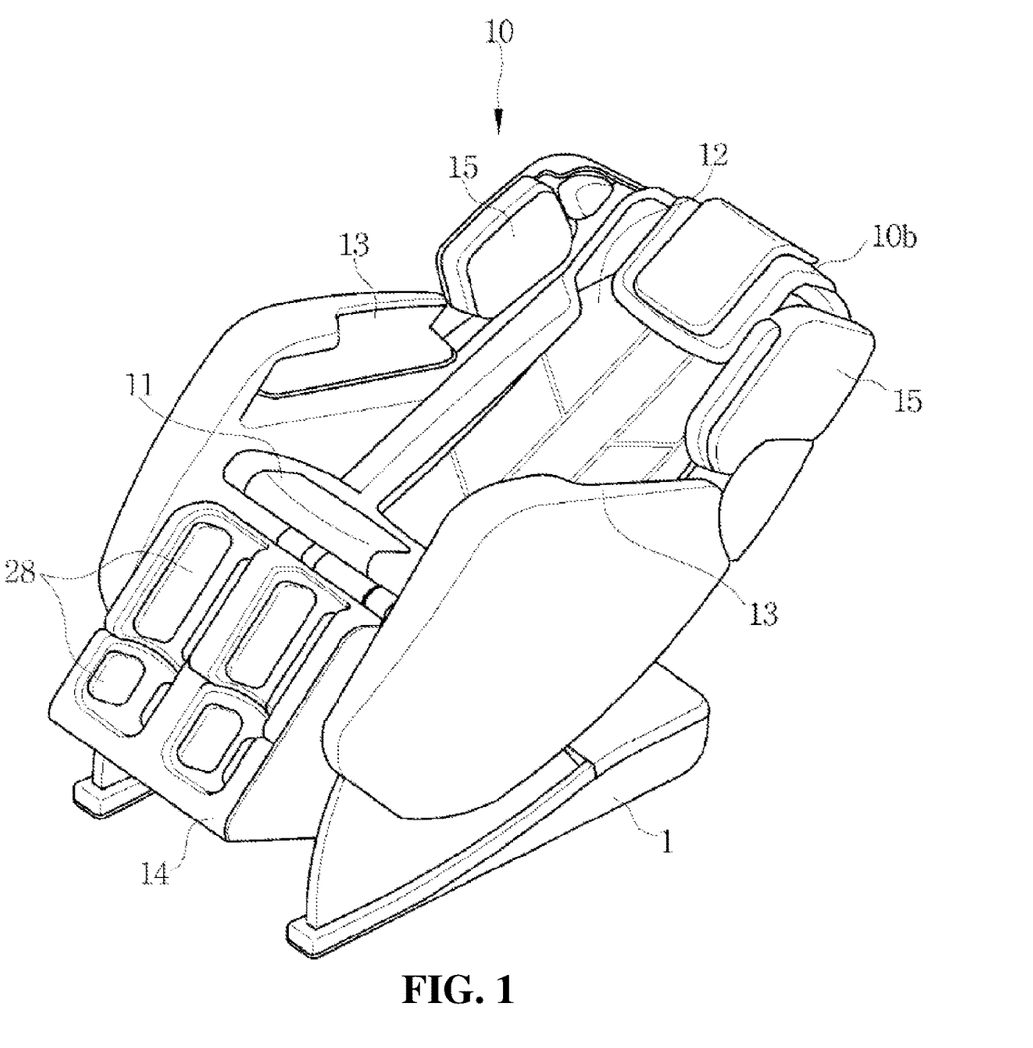
FIG. 1 is a perspective view of a massage apparatus providing a pulsed electromagnetic field according to an exemplary embodiment.
Figure 2:
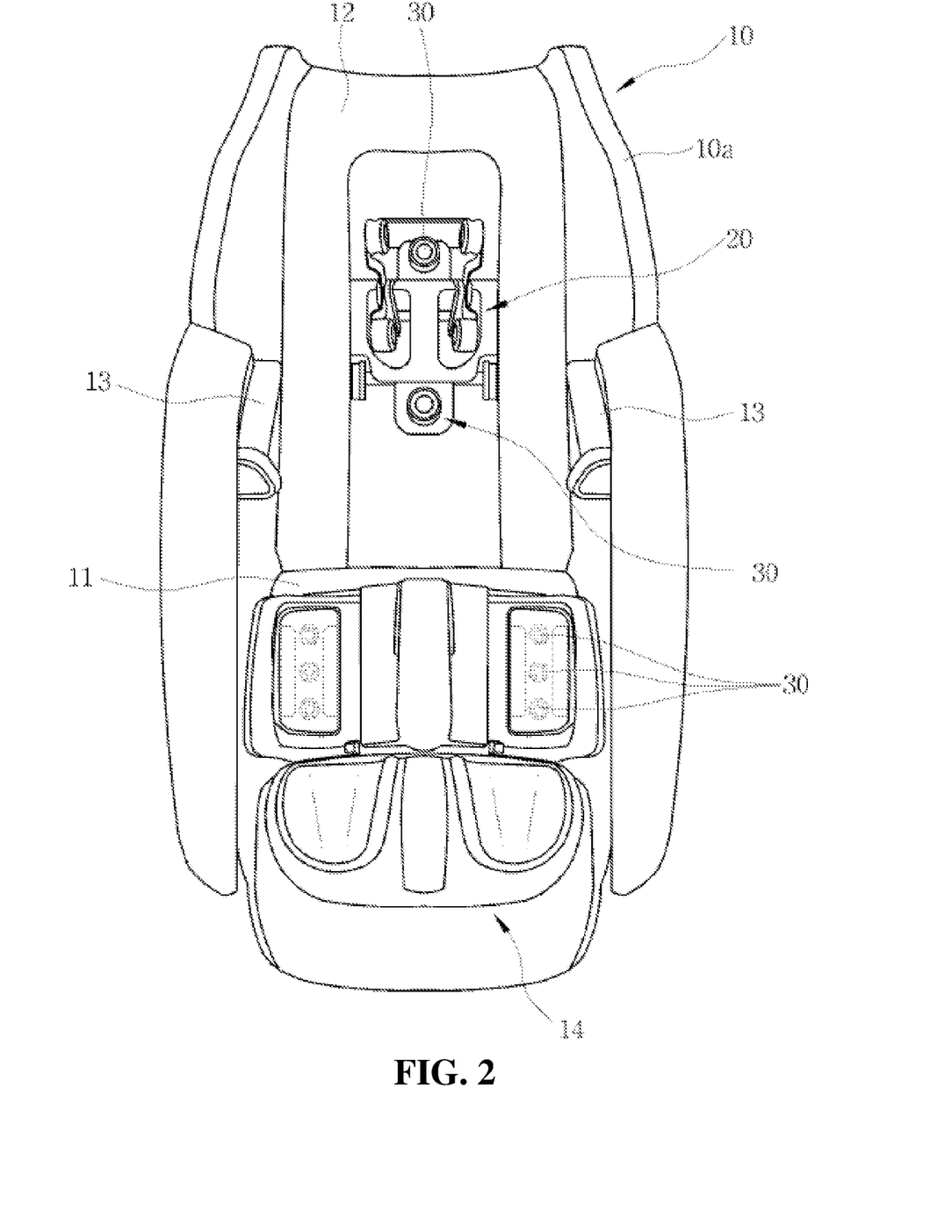
FIG. 2 is a front view of the massage apparatus illustrated in FIG. 1 with a covering material removed therefrom.

FIG. 1 is a perspective view of a massage apparatus providing a pulsed electromagnetic field according to an exemplary embodiment, and FIG. 2 is a front view of the massage apparatus illustrated in FIG. 1 with a covering material removed therefrom.

Referring to FIGS. 1 and 2, the massage apparatus includes a body 10 forming an exterior of the massage apparatus, a massage unit 20 for providing a pulsed electromagnetic field to a user sitting on the body 10 and performing a massaging operation and a controller 50 (see FIG. 11) for controlling operation of the massage unit 20. Here, the pulsed electromagnetic field means an electromagnetic field generated in pulse form according to an on or off state of power applied thereto.

The body 10 includes a housing 10a forming a frame of the massage apparatus and a covering material 10b provided so as to cover the housing 10a. In addition, the body 10 may include a seat part 11, a backrest part 12, a pair of left and right armrest parts 13, a leg massage part 14, and shoulder massage parts 15. Each of rear surfaces of the seat part 11, the backrest part 12, the armrest parts 13, the shoulder massage parts 15, and the leg massage part 14 may have the massage unit 20 for performing a massaging operation on each site of the user.

The massage unit 20 may perform a massaging operation by applying pressure to the body parts, for example, a back, shoulders, a neck, thighs, a pelvis, arms, and legs of the user sitting on the body 10 by tapping, massaging, or rubbing the body.

The massage unit 20 may be provided as a plurality of massage units 20. For example, the massage unit 20 may include massage units 20 corresponding to the seat part 11 and the backrest part 12, massage units 20 corresponding to the armrest parts 13, massage units 20 corresponding to the shoulder massage parts 15, and a massage unit 20 corresponding to the leg massage part 14.

The plurality of massage units 20 may be provided as mechanical massage units or pneumatic massage units. Here, the mechanical massage units mean massage units which have acupressure modules 23 for applying pressure to the user's body by means of a driving force of a motor, that is, mechanically actuated massage units, and the pneumatic massage units mean massage units which have air cells 28 repeatedly expanded and contracted by injection or withdrawn of air, that is, pneumatically actuated massage units.

The plurality of massage units 20 may be composed of only mechanical massage units or only pneumatic massage units or may be composed of a combination thereof. Merely, for convenience in explanation, the massage units 20 composed of the combination will be described hereinafter.

For example, as illustrated in FIG. 2, the massage units 20 corresponding to the seat part 11 and the backrest part 12 may be provided as mechanical massage units, and the massage units 20 corresponding to the armrest parts 13, the shoulder massage parts 15, and the leg massage part 14 may be provided as pneumatic massage units.

The massage units 20 provided inside the seat part 11 and the backrest part 12 are mechanical massage units and may perform a tapping operation or a massaging operation while moving on the seat part 11 and the backrest part 12 in a longitudinal direction of the housing 10a by driving forces of motors 22 and 43 (see FIG. 4) and may apply pressure to the body of the user sitting thereon.

Figure 3:
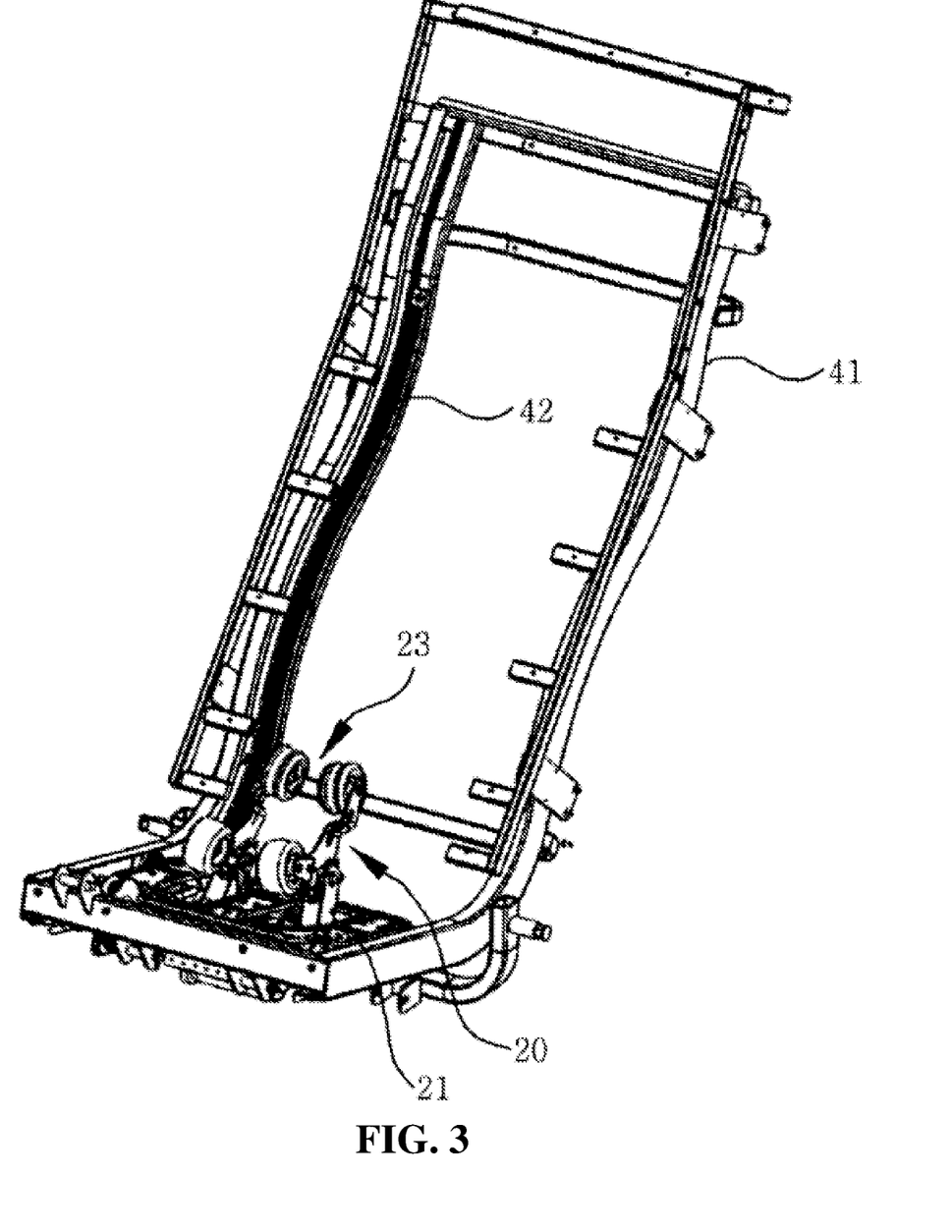
FIG. 3 is a view for describing operation of a mechanical massage unit.
Figure 4:
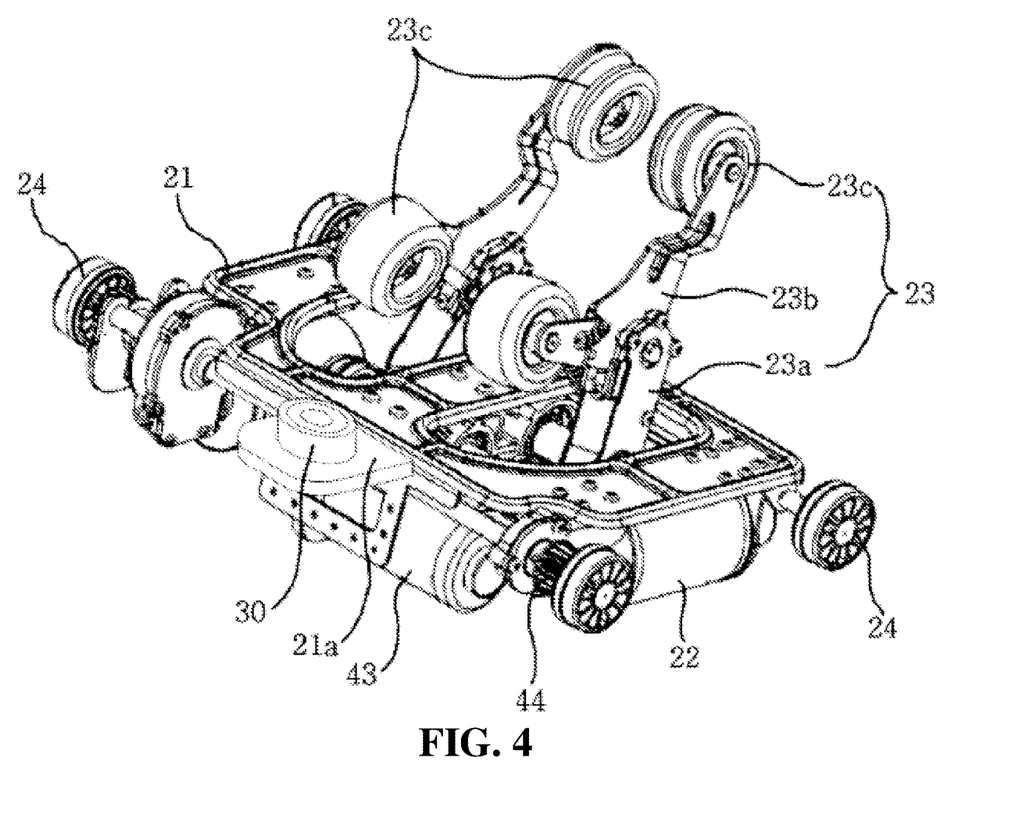
FIG. 4 is a view for describing a structure of the mechanical massage unit.

FIG. 3 is a view for describing operation of a mechanical massage unit, and FIG. 4 is a view for describing a structure of the mechanical massage unit.

Referring to FIGS. 3 and 4, the massage unit 20 may include a mount frame 21 provided so as to reciprocate between one location and the other location in the longitudinal direction of the housing 10a, the acupressure modules 23 provided on the mount frame 21 so as to reciprocate in response to movement of the mount frame 21 and apply pressure to the user's body, and a pulsed electromagnetic field generator 30 provided on the mount frame 21 so as to generate a pulsed electromagnetic field by means of power applied thereto.

For the movement of the mount frame 21, a rail frame 41 fixedly provided on the massage apparatus and a rack gear 42 provided along the inside of the rail frame 41 may be provided on a rear surface of the housing 10a, and the massage unit 20 may include pinion gears 44 provided on both sides of the mount frame 21 so as to be engaged with the rack gear 42 and rotated, and the motor 43 (hereinafter referred to as a "raising and lowering motor") for rotating the pinion gears 44. Thus, when the raising and lowering motor 43 is operated by power applied thereto, the pinion gears 44 are engaged with the rack gear 42 and rotated, and the mount frame 21 is moved along the rack gear 42 in a vertical direction.

The mount frame 21 has a quadrangular plate shape and has four wheels 24 formed on left and right edges thereof and laterally protruded so as to be fitted to the rail frame 41 and guided. Thus, as described above, when the operation of the raising and lowering motor 43 allows the pinion gears 44 to be engaged with the rack gear 42 and rotated, the wheels 24 are guided along the rail frame 41 so that the mount frame 21 may be moved smoothly. The shape of the mount frame 21 or the number of the wheels 24 is merely an example, and the embodiment of the inventive concept is not limited thereto.

The mount frame 21 may have the acupressure modules 23 provided to protrude from a front surface of the mount frame 21 so as to apply pressure to the user's body.

The acupressure module 23 may include swing levers 23a connected to shafts of motors 22 (hereinafter referred to as "swing motors") through a power transmission member, massage arms 23b supported by front ends of the swing levers 23a, and a plurality of massage rollers 23c supported by front ends of the massage arms 23b. Thus, upon operation of the swing motors 22, driving forces of the swing motors 22 move the swing motors 22 in a front-rear direction or a lateral direction, and the massage arms 23b and the massage rollers 23c perform a massaging operation, such as tapping or massaging, on the user's body while being operated in response to the movements of the swing levers 23a.

Further, as described above, a driving force of the raising and lowering motor 43 moves the mount frame 21 along the rack gear 42, and, in response to the movement of the mount frame 21, the acupressure module 23 is reciprocated. In this case, the massage arms 23b and the massage rollers 23c may perform a massaging operation, such as rubbing, on the user's body in a vertical direction.

The pulsed electromagnetic field generator 30 is provided on the mount frame 21 so as to generate a pulsed electromagnetic field while moving together with the mount frame 21, thereby providing, to the user's body, a treatment effect due to the pulsed electromagnetic field. A configuration of the pulsed electromagnetic field generator 30 will be described in more detail with reference to FIGS. 5 and 6.

Figure 5:
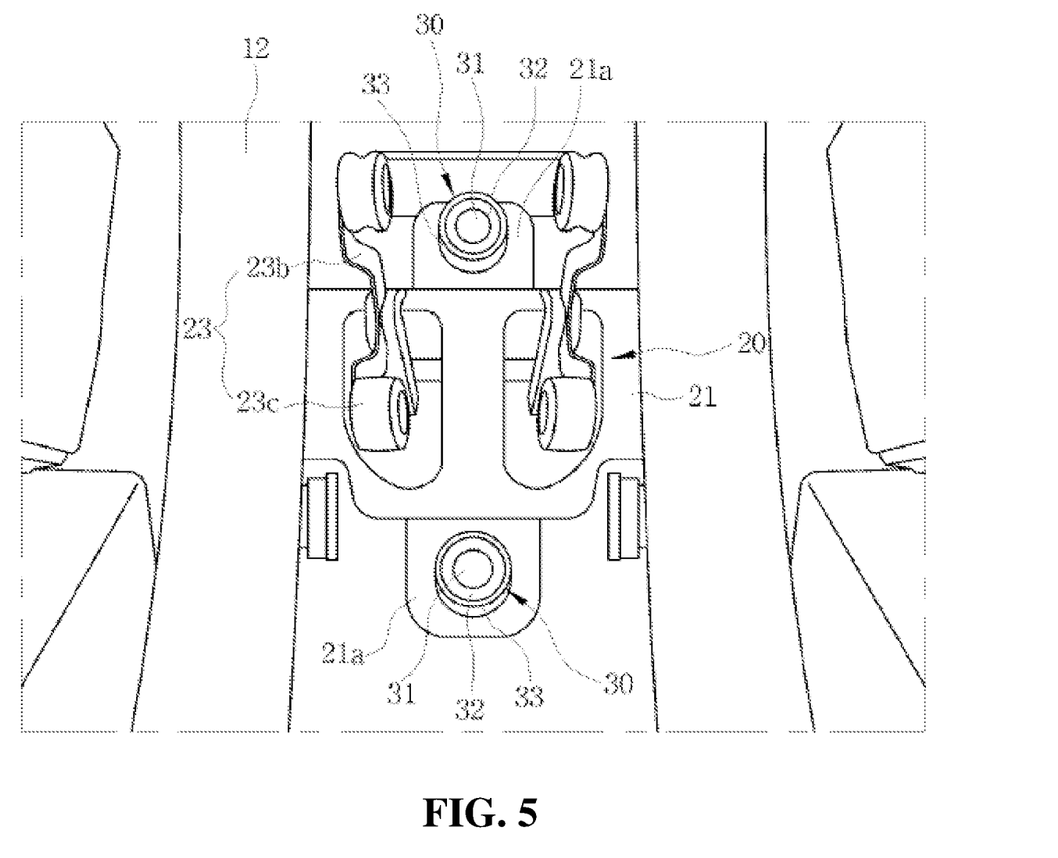
FIG. 5 is a front view of a massage unit in which a pulsed electromagnetic field generator is provided according to an exemplary embodiment.
Figure 6:
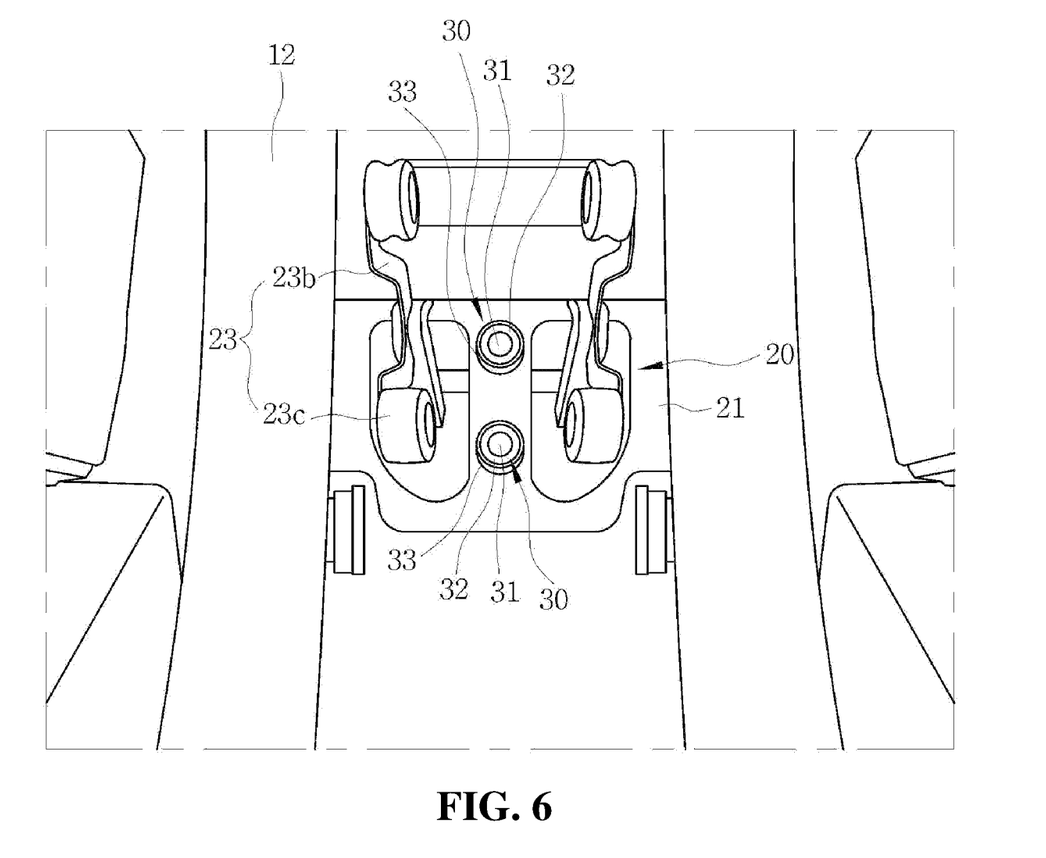
FIG. 6 is a front view of a massage unit in which a pulsed electromagnetic field generator is provided according to another exemplary embodiment.

FIG. 5 is a front view of a massage unit in which a pulsed electromagnetic field generator is provided according to an exemplary embodiment, and FIG. 6 is a front view of a massage unit in which a pulsed electromagnetic field generator is provided according to another exemplary embodiment.

Referring to FIGS. 5 and 6, the pulsed electromagnetic field generator 30 may be provided on the front surface of the mount frame 21 so as to generate a pulsed electromagnetic field in front of the mount frame 21.

The pulsed electromagnetic field generator 30 may be provided on the mount frame 21 independently of the acupressure modules 23. The pulsed electromagnetic field generator 30 may be disposed between the acupressure modules 23, that is, in a central portion of the mount frame 21, and, unlike that illustrated in the drawings, the pulsed electromagnetic field generator 30 may also be disposed on an outer side of the acupressure module 23 or on an upper or lower side thereof.

Further, the pulsed electromagnetic field generator 30 may be provided as a plurality of pulsed electromagnetic field generators 30 and may also be provided as a single pulsed electromagnetic field generator 30. When the pulsed electromagnetic field generator 30 may be provided as the plurality of pulsed electromagnetic field generators 30, the plurality of pulsed electromagnetic field generators 30 may be disposed at predetermined intervals in the vertical direction or the lateral direction. For example, as illustrated in FIG. 5, the plurality of pulsed electromagnetic field generators 30 may be provided on separate brackets 21a and spaced apart from each other. That is, the separate brackets 21a may be fixedly provided on an upper end portion and a lower end portion of the mount frame 21, and the pulsed electromagnetic field generators 30 may be provided on front surface portions of the brackets 21a. For another example, as illustrated in FIG. 6, the plurality of pulsed electromagnetic field generators 30 may also be directly provided on the mount frame 21 and spaced apart from each other.

Further, all of the plurality of pulsed electromagnetic field generators 30 may also be disposed between the acupressure modules 23. However, unlike that illustrated in the drawings, all of the pulsed electromagnetic field generators 30 may also be disposed on an outer side of the acupressure module 23, or a portion thereof may be disposed between the acupressure modules 23, and another portion thereof may also be disposed on the outer side of the acupresure module 23.

Further, the plurality of pulsed electromagnetic field generators 30 may be provided in the same size and shape and may also be provided in different sizes or shapes.

Figure 7:
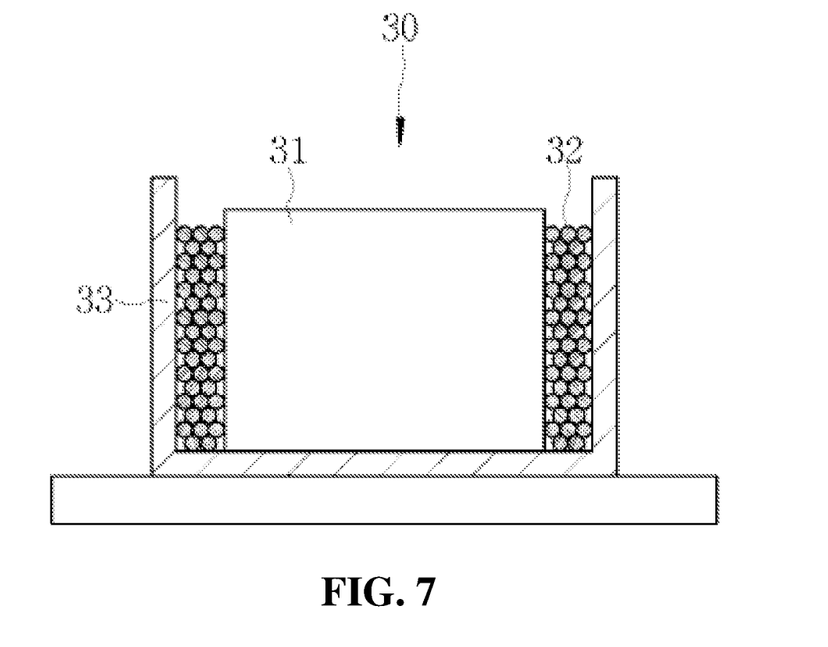
FIG. 7 is a cross-sectional view illustrating a shape of an electromagnetic field generator according to an embodiment.

FIG. 7 is a cross-sectional view illustrating a shape of an electromagnetic field generator according to an embodiment.

Referring to FIG. 7, the pulsed electromagnetic field generator 30 may have a structure in which an outer coil 32 is wound around an outer side of an inner core 31 having a cylindrical shape so as to allow a magnetic field to be induced in the inner core 31 by means of a pulse voltage applied to the outer coil 32, thereby generating a pulsed electromagnetic field.

The inner core 31 of the pulsed electromagnetic field generator 30 may be formed using a magnetic material such as ferrite. The outer coil 32 may be wound around an outer surface of the inner core 31, and a protective cover 33 formed as a nonconductor and having a ring shape may be provided on an outer side of the outer coil 32 so as to encompass the outer side of the inner core 31. However, the above description is merely an example, and as long as the pulsed electromagnetic field generator 30 may generate a pulsed electromagnetic field by means of a voltage applied thereto, various types of known pulsed electromagnetic field generators may be applied and configured.

Further, the pulsed electromagnetic field generator 30 may further include a guide member 35 (see FIG. 8) for guiding the generated pulsed electromagnetic field towards the user's body.

Figure 8:
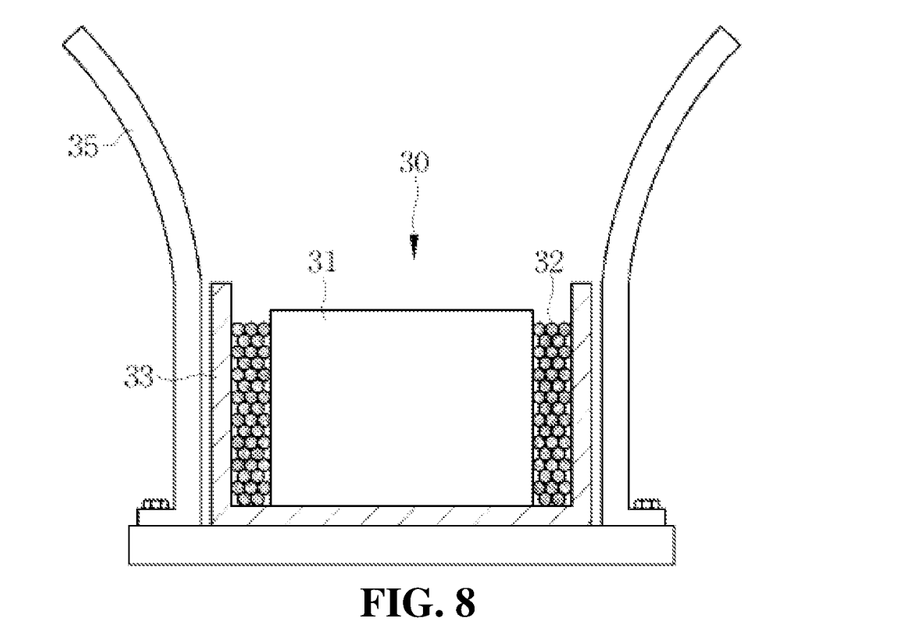
FIG. 8 is a cross-sectional view illustrating a shape of an electromagnetic field generator in which a guide member is provided according to an embodiment.

FIG. 8 is a cross-sectional view illustrating a shape of an electromagnetic field generator in which a guide member is provided according to an embodiment.

Referring to FIG. 8, the guide member 35 may be provided so as to encompass an outer side of the pulsed electromagnetic field generator 30. The guide member 35 may be provided in a cone shape with a diameter becoming greater towards the user's body such that the pulsed electromagnetic field generated by the pulsed electromagnetic field generator 30 is concentrated towards the user's body. The guide member 35 may also have a linear cone shape with a diameter becoming greater towards the user's body. However, as in this embodiment, it is more preferable for the guide member 35 to have a parabolic shape with a non-linearly increasing diameter that amplifies a pulsed electromagnetic field and provides the amplified pulsed electromagnetic field to the body parts.

As described above, the guide member 35 may be provided of a magnetic material, such as ferrite, or a metal, or formed of a ceramic material to block propagation of an electromagnetic field to the outside without interference of the operation of the acupressure module 23 as well as guiding the generated pulsed electromagnetic field towards the user's body.

The pulsed electromagnetic field generated by the pulsed electromagnetic field generator 30 increases the circulation of the blood to tissues of the user's body and the periphery thereof so as to supply more oxygen to the cells, thereby effectively helping to heal damaged cells, and providing effects such as activation of cells, stimulation of metabolism, and strengthening of immune system.

The pulsed electromagnetic field generator 30 may be provided on the mount frame 21 so as to provide a pulsed electromagnetic field effect to muscles and nerves around the spine while moving along the user's spinal line in response to the movement of the mount frame 21. The pulsed electromagnetic field generator 30 may be provided on the mount frame 21 together with the acupressure module 23 so that a pulsed electromagnetic field is provided to the user's body while the acupressure module 23 applies pressure to the user's body so as to perform tapping, massaging, or rubbing, thereby providing an effect of activating respective tissue cells or healing damaged cells of the body being massaged together with a massaging effect. The pulsed electromagnetic field generator 30 may highly increase the cell activating or healing effect by providing a pulsed electromagnetic field while the acupressure module 23 performs a massaging operation, as compared to when the pulsed electromagnetic field generator 30 provides only a pulsed electromagnetic field without a massaging operation or provides only a continuous electromagnetic field.

When the pulsed electromagnetic field generator 30 is disposed in the central portion of the mount frame 21, the pulsed electromagnetic field generator 30 may increase the cell activating or healing effect by providing a pulsed electromagnetic field to the user's meridian points, for example, great shuttle, wind gate, lung transporter, and jueyin transporter. Further, as compared to when the single pulsed electromagnetic field generator 30 is provided, when the plurality of pulsed electromagnetic field generators 30 are provided, the pulsed electromagnetic field effect may be further increased.

Further, the pulsed electromagnetic field generator 30 may be disposed on the mount frame 21 independently of the acupressure module 23 so as to provide a pulsed electromagnetic field to nearby sites to which pressure is not applied by the acupressure module 23, as well as body parts to which pressure is applied by the acupres sure module 23 and broaden the range of the healing effect due to the electromagnetic field. As the pulsed electromagnetic field generator 30 is independently disposed, the pulsed electromagnetic field generator 30 may be attached to the mount frame 21, detached from the mount frame 21, or replaced with new one independently of the acupressure module 23.

Referring again to FIG. 1, the massage units 20 provided as the pneumatic massage units to the armrest parts 13, the shoulder massage parts 15, and the leg massage part 14 may include the air cells 28 repeatedly expanded and contracted by injection and withdrawal of air so as to apply pressure to the arms, shoulders, legs, and the like of the user sitting thereon.

Figure 9:
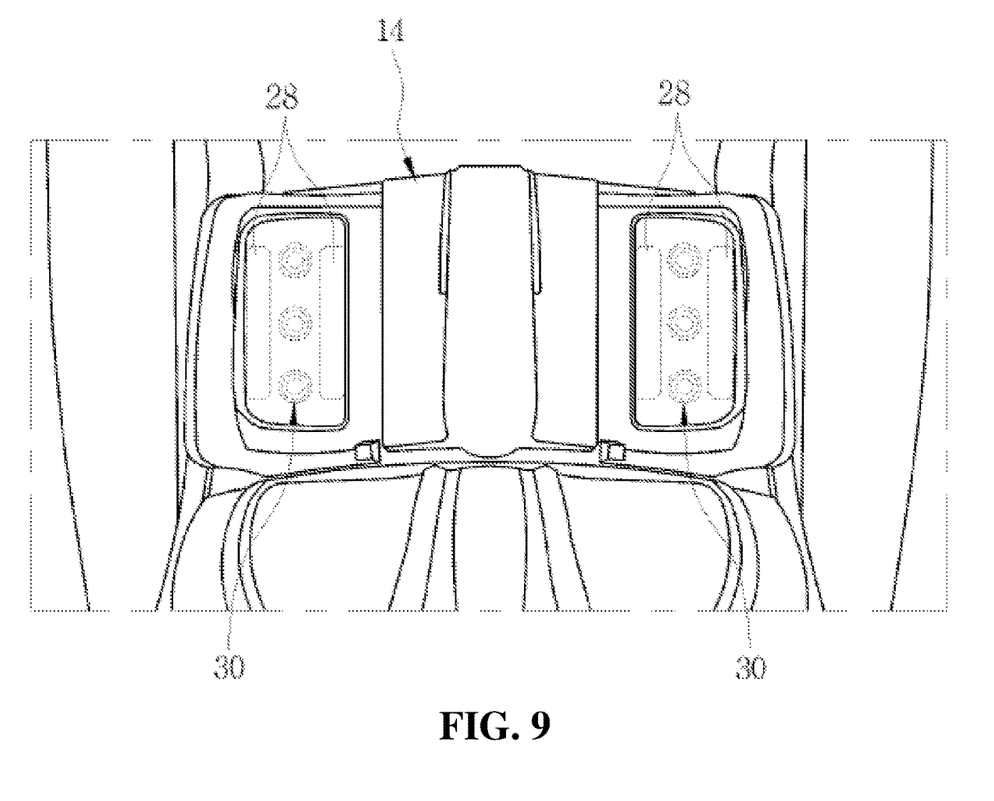
FIG. 9 is a front view of a leg massage part on which a pneumatic massage unit is provided according to an exemplary embodiment.
Figure 10:
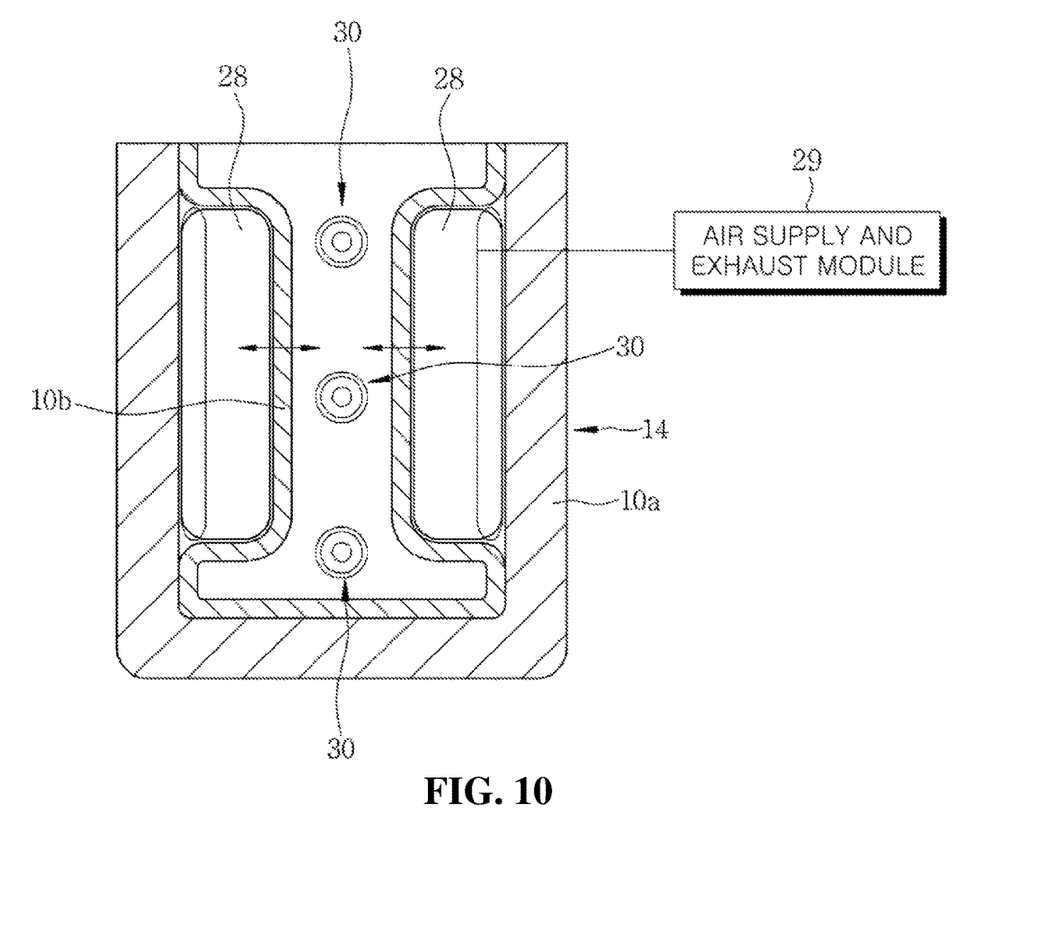
FIG. 10 is a cross-sectional view of the leg massage part on which the pneumatic massage unit is provided according to the exemplary embodiment.

FIG. 9 is a front view of a leg massage part on which a pneumatic massage unit is provided according to an exemplary embodiment, and FIG. 10 is a cross-sectional view of the leg massage part on which the pneumatic massage unit is provided according to the exemplary embodiment.

Referring to FIGS. 9 and 10, the massage unit 20 may include the air cells 28 provided in the housing 10*a* so as to apply pressure to the body while being repeatedly expanded and contracted by injection and withdrawal of air, an air supply and exhaust module 29 for performing operations of injecting air into and withdrawing air from the air cells 28, and the pulsed electromagnetic field generator 30 provided on the rear surface of the housing 10*a*.

The air cells 28 may be provided on the housing 10*a*, may also be provided on a rear surface of the covering material 10*b*, and may also be detachably provided on a front surface of the covering material 10*b* from the covering material 10*b*. The air cells 28 may perform a massaging operation by applying pressure to the body while being repeatedly expanded by air supplied from the air supply and exhaust module 29 and contracted by an air suction force generated by the air supply and exhaust module 29.

Known various air supply and exhaust modules may be used as the air supply and exhaust module 29 including a pneumatic pump for compressing and supplying air, a flow control valve for controlling supply of air from the pneumatic pump to the air cells 28, and the like.

The pulsed electromagnetic field generator 30 may be fixedly provided on the rear surface of the housing 10*a* so as to provide a pulsed electromagnetic field to the user's body. The pulsed electromagnetic field generator 30 may also be directly provided on the rear surface of the housing 10*a* and may also be provided on a support frame encompassed by the housing 10*a* and supporting the housing 10*a*.

The pulsed electromagnetic field generator 30 may be disposed between the air cells 28, and unlike that illustrated in the drawings, the pulsed electromagnetic field generator 30 may also be disposed on outer sides of the air cells 28 or on upper or lower sides thereof. When the pulsed electromagnetic field generator 30 is provided as the plurality of pulsed electromagnetic field generators 30, all of the plurality of pulsed electromagnetic field generators 30 may also be disposed between the air cells 28. In contrast, all of the pulsed electromagnetic field generators 30 may also be disposed on the outer sides of the air cells 28, or a portion thereof may be disposed between the air cells 28, and a portion thereof may also be disposed on the outer sides of the air cells 28 or on the upper or lower sides thereof.

Further, the plurality of pulsed electromagnetic field generators 30 may be provided in the same size and shape and may also be provided in different sizes or shapes.

As described above, in the case of the pneumatic massage unit, the massage unit 20 includes the pulsed electromagnetic field generator 30 together with the air cells 28, and the air cells 28 may provide a pulsed electromagnetic field effect to wrist joints, shoulder joints, knee joints, ankle joints, and the like while the air cells 28 apply pressure to the user's arms, shoulders, legs, and the like.

The pulsed electromagnetic field generator 30 may be disposed independently of the air cells 28 so as to broaden the range of the healing effect due to an electromagnetic field, including providing the pulsed electromagnetic field to even nearby sites to which pressure is not applied by the air cells 28 and to be attached to the pneumatic massage unit, detached from the pneumatic massage unit, or replaced with new one independently of the air cells 28.

Figure 11:
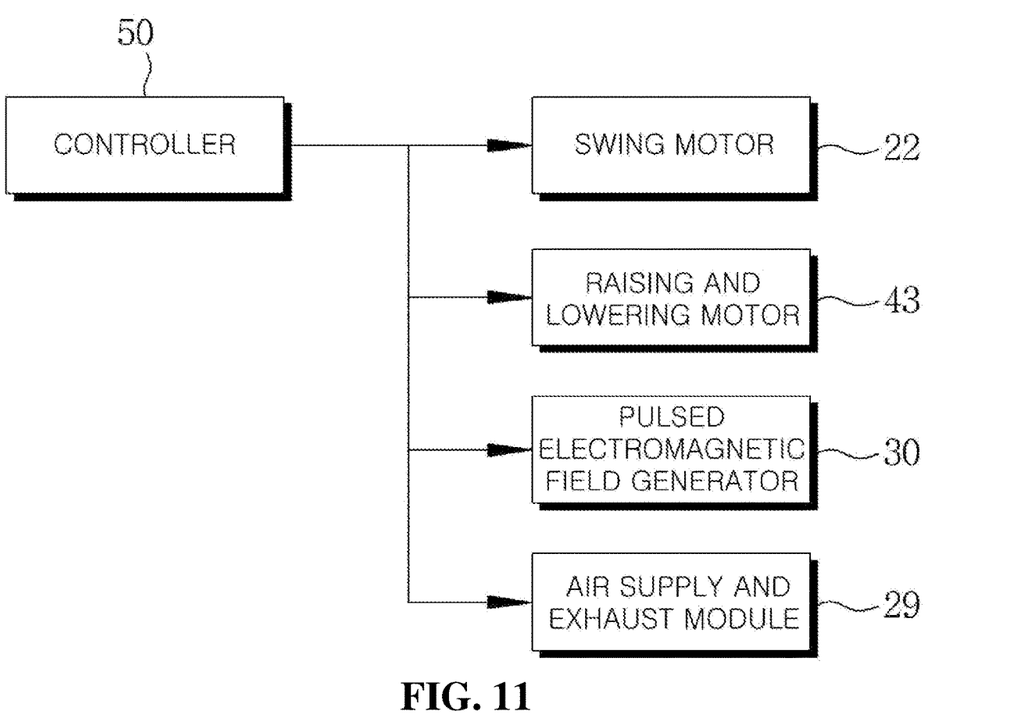
FIG. 11 is a block diagram illustrating a configuration for control of a massage apparatus.

The pulsed electromagnetic field generator 30 generates a pulsed electromagnetic field while being turned on or off under the control of a controller 50 (see FIG. 11). The controller 50 will be described in more detail with reference to FIG. 11.

FIG. 11 is a block diagram illustrating a configuration for control of a massage apparatus.

Referring to FIG. 11, the controller 50 may control operations of the swing motors 22, the raising and lowering motor 43, the pulsed electromagnetic field generator 30, and the air supply and exhaust module 29.

The controller 50 may drive the swing motors 22 and the raising and lowering motor 43 so as to control reciprocating of the massage unit 20 in a front-rear direction, a lateral direction, or a vertical direction. The controller 50 may control injection and withdrawal of air by the air supply and exhaust module 29.

The controller 50 may apply power to the pulsed electromagnetic field generator 30 so as to control generation of a pulsed electromagnetic field and a pulse signal. The controller 50 may control an on or off state, an on or off time, strength, and the like of power applied to the pulsed electromagnetic field generator 30 so as to control at least one among a time when a pulsed electromagnetic field is generated, a time when the generation thereof is terminated, a frequency, a period, a width, an intensity, and a shape thereof.

The controller 50 may control the power applied to the pulsed electromagnetic field generator 30 in conjunction with operation of the swing motors 22, the raising and lowering motor 43, or the air supply and exhaust module 29 such that, while the acupressure module 23 of the massage unit 20 or the air cells 28 perform a massaging operation, a pulsed electromagnetic field is generated. It is confirmed that it is preferable that, when the massage unit 20 performs a massaging operation, the pulsed electromagnetic field generator 30 receives a pulse signal from the controller 50 and generates a pulsed electromagnetic field of about 5 to 15 Hz, and it is most preferable that the pulsed electromagnetic field generator 30 generates a pulsed electromagnetic field of 14.1 Hz in terms of providing, to the body, an effect of activating and healing cells.

The controller 50 may adjust the power applied to the pulsed electromagnetic field generator 30 according to a location, a moving speed, a massage mode, an elapsed massage time, and the like of the massage unit 20 so as to provide a controlled pulsed electromagnetic field according to the user's body parts, the massage mode, and the elapsed massage time. That is, the controller 50 may control the pulsed electromagnetic field generator 30 such that the pulsed electromagnetic field generator 30 provides a pulsed electromagnetic field having optimum conditions such as a frequency, a period, a width, and an intensity thereof according to the location, the moving speed in the up-to-down direction, the massage mode, the elapsed massage time, and the like of the massage unit 20.

To this end, the controller 50 may include a switching output device for outputting magnetic field pulse energy to the outer coil 32 of the pulsed electromagnetic field generator 30, a signal control unit for generating a control pulse signal to be applied to an input of the switching output device, a switching regulator for supplying stable power, an input/output (I/O) port, and a power supply. In this case, the signal control unit as a part for generating a series of pulses to drive the switching output device may allow a micro controller built therein to calculate the optimum conditions such as the frequency, the period, the width, and the intensity and generate and output a pulse signal.

The exemplary embodiments of the massage apparatus providing a pulsed electromagnetic field have been described with reference to the exemplified drawings, but it would be understood by those skilled in the art that various changes and modifications can be made without changing the technical concept or essential features of the disclosure. Thus, it should be understood that the above-described embodiments are illustrative in all aspects and do not limit the disclosure.

INDUSTRIAL APPLICABILITY

The disclosure is applicable to a massage chair or a massage apparatus having a massage function.

The invention claimed is:

1. A massage apparatus that provides a pulsed electromagnetic field, the massage apparatus comprising:
    a massage unit comprising:
        a mount frame provided to be movable along the massage apparatus;
        a plurality of acupressure modules provided to protrude from the mount frame and to apply pressure to a body of a user; and
        one or more swing motors; and
    a pulsed electromagnetic field generator provided on the mount frame independently of the plurality of acupressure modules and configured to generate the pulsed electromagnetic field by power applied thereto,
    wherein each of the plurality of acupressure modules comprises:
        one or more massage rollers applying the pressure to the body of the user;
        a swing lever connected to a shaft of the one or more swing motors at one end thereof; and
        a massage arm connected to an other end of the swing lever and supporting the one or more massage rollers,
    wherein when the one or more swing motors are operated, a driving force of the one or more swing motors move the swing levers in a lateral direction and the massage rollers perform a massaging operation in the lateral direction,
    wherein at least some of the plurality of the acupressure modules are disposed to be spaced apart from each other in the lateral direction, and the pulsed electromagnetic field generator is disposed in an area between the spaced apart acupressure modules, and
    wherein the pulsed electromagnetic field generator comprises:
        a cylindrical inner core;
        an outer coil wound around an outer circumferential surface of the cylindrical inner core and inducing the pulsed electromagnetic field in the inner core by a pulse voltage applied to the outer coil;
        a protective cover surrounding an outer side of the outer coil; and
        a guide member surrounding an outer side of the protective cover,
        wherein a height of the guide member is greater than a height of the protective cover, and a diameter of the guide member increases towards the body of the user.

2. The massage apparatus of claim 1, wherein the pulsed electromagnetic field generator is provided as a plurality of pulsed electromagnetic field generators, and the plurality of pulsed electromagnetic field generators are disposed spaced apart from each other at predetermined intervals.

3. The massage apparatus of claim 2, wherein the plurality of pulsed electromagnetic field generators includes pulsed electromagnetic field generators having different sizes or shapes.

4. The massage apparatus of claim 1, further comprising a fixed rail frame and a rack gear disposed along an inside of the rail frame,
wherein the massage unit further comprises:
a raising and lowering motor; and
pinion gears disposed on sides of the mount frame and configured to engage with the rack gear and rotate by a driving force of the raising and lowering motor,
wherein when the raising and lowering motor is operated, the mount frame is moved along the rack gear in a vertical direction, and the massage arms and the massage rollers perform a massaging operation in the vertical direction.

5. The massage apparatus of claim 1, further comprising a controller configured to control operation of the plurality of acupressure modules and generation of the pulsed electromagnetic field,
wherein the controller is configured to control the power applied to the pulsed electromagnetic field generator according to a location and a moving speed of the massage unit and the pulsed electromagnetic field is controlled depending on a body part of the user to which the pulsed electromagnetic field is applied.

6. The massage apparatus of claim 5, wherein the controller controls at least one among a time when the pulsed electromagnetic field is generated, a time when the generation of the pulsed electromagnetic field is terminated, a frequency, a period, a width, an intensity, and a shape thereof.

7. The massage apparatus of claim 6, wherein the controller controls the generation of the pulsed electromagnetic field in conjunction with the operation of the plurality of acupressure modules.

8. The massage apparatus of claim 6, wherein the controller controls the generation of the pulsed electromagnetic field on the basis of at least one among a location, a moving speed, a massage mode, and an elapsed massage time of the massage unit.

9. The massage apparatus of claim 6, wherein the controller controls the generation of the pulsed electromagnets field at a frequency of 5 to 15 Hz.

10. A massage apparatus that provides a pulsed electromagnetic field, the massage apparatus comprising:
an air cell provided in a housing and applying pressure to a body of a user while being repeatedly expanded and contracted by air;
a pulsed electromagnetic field generator provided on a rear surface of the housing independently of the air cell and configured to generate a pulsed electromagnetic field by means of power applied thereto; and
a controller configured to control operation of the air cell and generation of the pulsed electromagnetic field,
wherein the pulsed electromagnetic field generator comprises:
a cylindrical inner core;
an outer coil wound around an outer circumferential surface of the cylindrical inner core and inducing the pulsed electromagnetic field in the inner core by a pulse voltage applied to the outer coil;
a protective cover surrounding an outer side of the outer coil; and
a guide member surrounding an outer side of the protective cover,
wherein a height of the guide member is greater than a height of the protective cover, and a diameter of the guide member increases towards the body of the user.

11. A massage apparatus that provides a pulsed electromagnetic field, the massage apparatus comprising:
a massage unit including a mount frame provided to be movable along the massage apparatus and acupressure modules provided to protrude from the mount frame and to apply pressure to a body of a user;
a pulsed electromagnetic field generator provided on the mount frame independently of the acupressure modules and configured to generate the pulsed electromagnetic field by power applied thereto; and
a controller configured to control operation of the acupressure modules and generation of the pulsed electromagnetic field,
wherein the pulsed electromagnetic field generator comprises:
a cylindrical inner core;
an outer coil wound around an outer circumferential surface of the cylindrical inner core and inducing the pulsed electromagnetic field in the inner core by a pulse voltage applied to the outer coil;
a protective cover surrounding an outer side of the outer coil; and
a guide member surrounding an outer side of the protective cover,
wherein a height of the guide member is greater than a height of the protective cover, and a diameter of the guide member increases towards the body of the user.

12. The massage apparatus of claim 11, wherein the pulsed electromagnetic field generator is provided as a plurality of pulsed electromagnetic field generators, and the plurality of pulsed electromagnetic field generators are disposed spaced apart from each other at predetermined intervals.

13. The massage apparatus of claim 12, wherein the plurality of pulsed electromagnetic field generators includes pulsed electromagnetic field generators having different sizes or shapes.

14. The massage apparatus of claim 11, wherein the controller controls at least one among a time when the pulsed electromagnetic field is generated, a time when the generation of the pulsed electromagnetic field is terminated, a frequency, a period, a width, an intensity, and a shape thereof.

15. The massage apparatus of claim 11, wherein the controller controls the generation of the pulsed electromagnetic field in conjunction with the operation of the acupressure modules.

16. The massage apparatus of claim 11, wherein the controller controls the generation of the pulsed electromagnetic field based on at least one among a location, a moving speed, a massage mode, and an elapsed massage time of the massage unit.

17. The massage apparatus of claim 11, wherein the controller controls the generation of the pulsed electromagnetic field at a frequency of 5 to 15 Hz is generated.

* * * * *